(12) United States Patent
Abboud

(10) Patent No.: US 8,814,568 B2
(45) Date of Patent: Aug. 26, 2014

(54) DENTAL JAW IMPLANT TO AFFIX DENTURES

(76) Inventor: Marcus Abboud, Setauket, NY (US)

( * ) Notice: Subject to any disclaimer, the term of this patent is extended or adjusted under 35 U.S.C. 154(b) by 0 days.

(21) Appl. No.: 13/401,870

(22) Filed: Feb. 22, 2012

(65) Prior Publication Data

US 2012/0214131 A1    Aug. 23, 2012

(30) Foreign Application Priority Data

Feb. 23, 2011    (DE) .......................... 10 2011 012 212

(51) Int. Cl.
*A61C 8/00*      (2006.01)
*A61C 5/08*      (2006.01)

(52) U.S. Cl.
CPC ................. *A61C 5/08* (2013.01); *A61C 8/0018* (2013.01); *A61C 8/00* (2013.01); *A61C 8/0069* (2013.01)
USPC .......................................... 433/173; 433/174

(58) Field of Classification Search
CPC .......... A61C 8/0069; A61C 5/08; A61C 8/00; A61C 8/0022; A61C 8/0075; A61C 8/0074; A61C 8/0045
USPC .................................................. 433/172–174
See application file for complete search history.

(56) References Cited

U.S. PATENT DOCUMENTS

| 4,976,739 | A  | * | 12/1990 | Duthie, Jr. ...................... 606/60 |
| 2002/0090593 | A1 | * | 7/2002 | Palti et al. ...................... 433/174 |
| 2004/0029075 | A1 | * | 2/2004 | Peltier et al. ................... 433/173 |
| 2008/0280254 | A1 | * | 11/2008 | Ackermann ................... 433/174 |
| 2011/0306015 | A1 | * | 12/2011 | Chen ............................. 433/173 |

* cited by examiner

*Primary Examiner* — Eric Rosen
(74) *Attorney, Agent, or Firm* — Norman B. Thot

(57) ABSTRACT

A dental jaw implant for supporting at least one of a replacement tooth neck and a crown portion includes a monolithic implant body comprising an ingrowth section comprising an ingrowth structure which grows together with a patient's jaw bone. An insertion opening is arranged at a coronal axial end. A replacement tooth neck and/or a crown portion is inserted in the insertion opening. A female thread adjoins the insertion opening. The female thread threads a replacement tooth retaining element. The replacement tooth retaining element retains the at least one of the replacement tooth neck and the crown portion. An outer cone is arranged at the coronal axial end. The outer cone tapers towards a non-coronal end. A radial step comprises an annular surface substantially disposed in a radial plane. The annular surface is arranged between the outer cone and the ingrowth section.

20 Claims, 2 Drawing Sheets

DENTAL JAW IMPLANT TO AFFIX DENTURES

CROSS REFERENCE TO PRIOR APPLICATIONS

Priority is claimed to German Patent Application No. DE 10 2011 012 212.5, filed Feb. 23, 2011. The entire disclosure of said application is incorporated by reference herein.

FIELD

The present invention provides a dental jaw implant for supporting a dental prosthesis.

BACKGROUND

A dental jaw implant is that part of a dental implant arrangement that is placed immediately in the jaw of a patient and comprises an insertion opening for retaining a separate neck portion of a replacement tooth and/or a separate crown portion of a replacement tooth. A permanently firm seating of the implant body in a patient's jaw is of utmost importance for the strength and the durability of the entire implant arrangement. In the interest of avoiding retention losses, it is desirable to avoid, as far as possible, force and tension peaks in the area of a patient's jaw in the event of the application of force on the implant body, for instance, during chewing.

SUMMARY

An aspect of the present invention is to provide a dental jaw implant with a good retention behavior.

In an embodiment, the present invention provides a dental jaw implant for supporting at least one of a replacement tooth neck and a crown portion which includes a monolithic implant body comprising an ingrowth section comprising an ingrowth structure configured to grow together with a patient's jaw bone. An insertion opening is arranged at a coronal axial end. The insertion opening is configured to have at least one of a replacement tooth neck and a crown portion be inserted therein. A female thread adjoins the insertion opening. The female thread is configured to thread a replacement tooth retaining element. The replacement tooth retaining element is configured to retain the at least one of the replacement tooth neck and the crown portion. An outer cone is arranged at the coronal axial end. The outer cone tapers towards a non-coronal end. A radial step comprises an annular surface substantially disposed in a radial plane. The annular surface is arranged between the outer cone and the ingrowth section.

BRIEF DESCRIPTION OF THE DRAWINGS

The present invention is described in greater detail below on the basis of embodiments and of the drawings in which.

DETAILED DESCRIPTION

Figure 1:
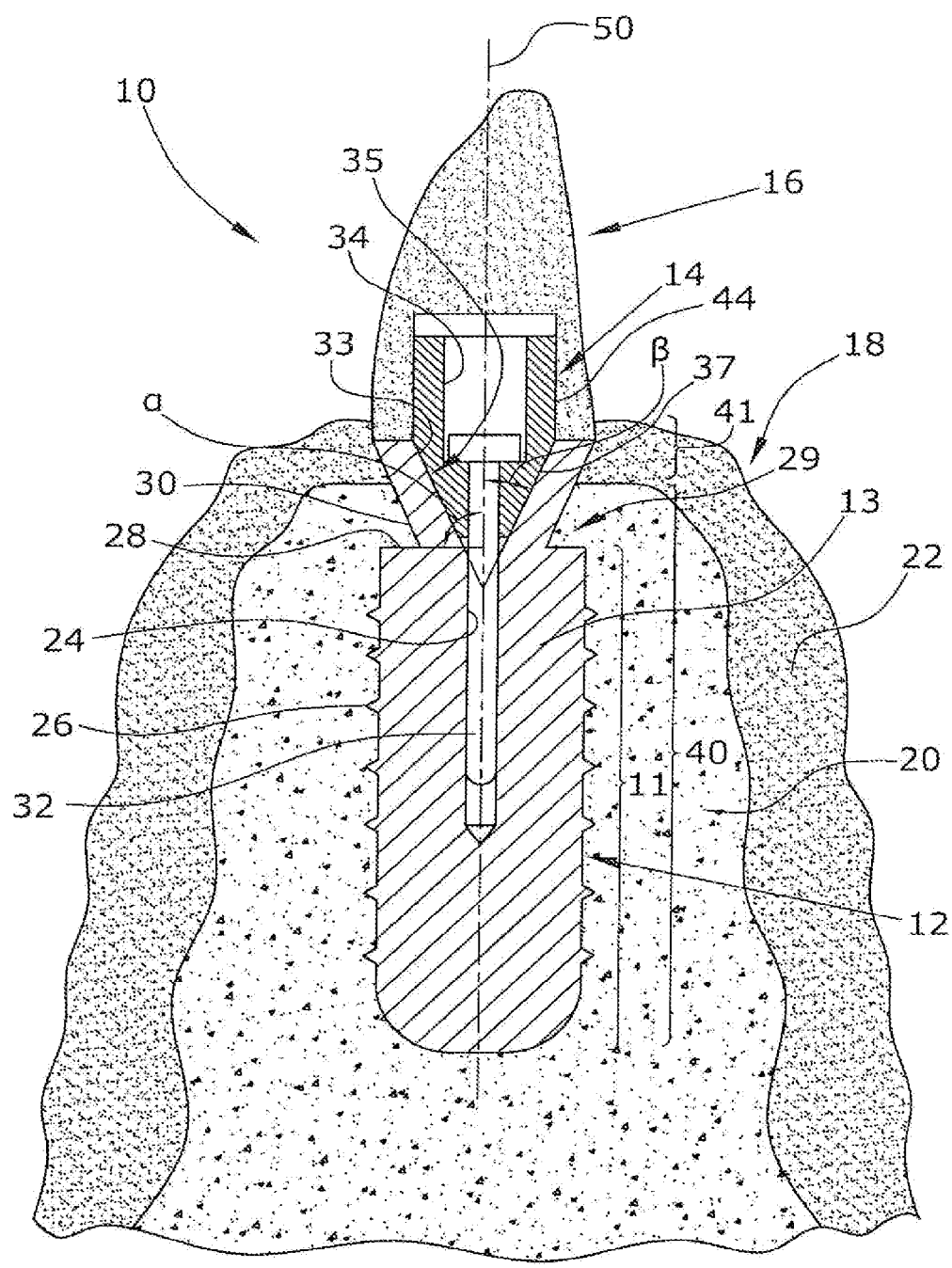
FIG. 1 shows a longitudinal section of an embodiment of a linear dental jaw implant implanted in a patient's jaw, the implant being provided with a neck portion and a crown portion of a replacement tooth.

In an embodiment of the present invention, the dental jaw implant comprises a monolithic implant body, wherein the implant body has an ingrowth section with an ingrowth structure for growing together with a patient's jaw. The ingrowth structure may, for example, consist of a cylindrical section with a single thread or multiple threads. The ingrowth structure may also consist of a plurality of cylindrical sections whose outer diameter gradually decreases towards the non-coronal end of the implant body. The ingrowth structure may also be conical in shape and/or have a smooth surface, the structure being provided in the form of indentations.

The coronal axial end of the implant body is provided with an insertion opening for the insertion of a neck portion or a crown portion of a replacement tooth. The insertion opening may be of a cylindrical, a conical or any other shape and substantially serves the lateral fixation of the inserted neck or crown portion. Adjoining the insertion opening in the non-coronal direction is a female thread for screwing thereinto a replacement tooth retaining element with which the neck or crown portion of the replacement tooth can be fixed to the implant body. The retaining element may be a retaining screw.

An outer cone is arranged at the axial coronal end of the implant body, which outer cone tapers to the non-coronal end. The cone angle of the outer cone can, for example, be 10°-50° to the axial line of the insertion opening. A radial step is also provided whose annular surface is substantially located in a radial plane, the radial step connecting the non-coronal end of the outer cone with the ingrowth section whose diameter is larger at that site than the non-coronal end of the outer cone.

The implant body thus has an external circumferentially extending inward directed step at its coronal end, which, in the form of the outer cone, widens towards the insertion opening to approximately the outer diameter of the ingrowth section at the axial portion adjoining the outer cone.

The radial step, where the implant body has a circular constriction, is arranged in the region of the patient's jaw bone, not in the area of the gingiva of the patient's jaw bone. As a consequence, the outer cone is also partly arranged in the patient's jaw and partly in the gingiva, when the jaw implant is implanted in the patient's jaw. Compared with a cylinder, the outer cone has a significantly larger surface, depending on the cone angle. Due to the outer cone, the forces applied via the neck and/or crown portion of the replacement tooth are further transmitted to the jaw bone under a more favorable angle of force induction, i.e., approximately vertically to the outer cone at the respective site. The more favorable angle of force induction and the larger force transmission surface causes a reduction of the force and tension peaks at the implant body/jaw bone interface. This, in turn, reduces the risk of pressure-related retention losses at the jaw bone.

In an embodiment of the present invention, the annular surface of the radial step can, for example, have an angle of 70°-100° with respect to the axial line of the insertion opening; the angle can, for example, be between 85° and 100°. This refers to the coronal angle between the annular surface and the axial line of the insertion opening, so that the cone angle of the outer cone falls entirely into the angle of the annular surface.

In an embodiment of the present invention, the outer cone can, for example, have a cone angle of 10°-50° with respect to the axial line of the insertion opening, the cone angle further being generally determined by the fact that the axial length of the outer cone is predefined as being, for example, about 3-5 mm. The angle between the outer cone and the annular surface of the radial step is thus between 90° and 20°, but should typically be between 80° and 50°.

In an embodiment of the present invention, the radial depth of the radial step can, for example, be at least one third of the largest outer diameter of the ingrowth section. If possible, the radial depth of the radial step should be at least 1.0 mm to allow a cone angle of the outer cone of more than 10°.

In an embodiment of the present invention, the radial step can, for example, be situated in a longitudinal jaw bone section of the implant body, i.e., in the longitudinal section which, when the implant body is implanted in the patient's jaw, is in the jaw bone and is surrounded by the jaw bone. After the implant body has been implanted in the jaw bone of a patient, the jaw bone grows radially inward into the radial step. The implant body is thereby anchored in the jaw bone in an axial coronal direction.

In an embodiment of the present invention, the outer cone can, for example, be partly situated in the longitudinal jaw bone section and partly in a longitudinal gingiva section of the implant body. The insertion opening at the coronal end of the outer cone is thus situated in the longitudinal gingiva section of the implant body, i.e., the longitudinal section that is situated in the gingiva of the patient's jaw after the implant body has been implanted.

In an embodiment of the present invention, the insertion opening can, for example, be angled with respect to the ingrowth section, i.e., the axial line is not parallel to the axial line of the ingrowth section, but angled relative thereto. The angle between the two axial lines can, for example, be between 165° and 110°, or for example, between 155° and 125°. A jaw implant can thus be provided that is implanted obliquely in the patent's jaw in order to avoid lesions of nerve tracts in the patient's jaw, i.e., it is not implanted vertically, but with a horizontal component.

FIG. 1 illustrates a longitudinal section through a dental implant arrangement 10 for insertion in a patient's jaw that is formed by a patient's jaw 18 and a dental implant arrangement which in turn comprises a linear jaw implant 12, a replacement tooth neck portion 14 and a replacement tooth crown portion 16.

The patient's jaw 18 is formed by a jaw bone 20 and the gingiva 22 surrounding the jaw bone 20.

The jaw implant 12 comprises a monolithic implant body 13 of titanium, but may also be made of zirconium oxide or a plastic material composite. The implant body 13 has two longitudinal implantation sections along its longitudinal direction, i.e., a longitudinal jaw bone section 40 sitting in the jaw bone 20 and a longitudinal gingiva portion 41 sitting in the gingiva 22. In the longitudinal jaw bone section 40, the implant body 13 comprises a cylindrical ingrowth section 11 which has a thread as its ingrowth structure 26. The ingrowth section 11 has an outer diameter of approximately 3.0 to 7.0 mm. The length of the implant body 13 may be between 8 and 35 mm.

In an embodiment of the present invention, the thread can, for example, be of the self-tapping type and as such comprises one, two or more cutting edges. As an alternative or in addition, the ingrowth section 11 may also be self-drilling or self-compacting. At its end directed to the jaw, the ingrowth section 11 may taper towards that end. The thread may be a single or a double thread. The pitch of the thread may be a constant pitch over the entire length of the ingrowth section 11, but it may also have a pitch that varies along the length of the thread. The pitch of the thread may be between 30° and 65°, for example, about 60°. The distance between two turns of the thread is 0.5-1.4 mm, for example, 1.3 mm.

At its coronal end, the ingrowth section 11 terminates in a radial step 29 formed by an annular surface 28. The annular surface has a radial depth of 0.25 to 1.0 mm and forms an angle α of 90° with the axial line 50. The radial step 29 is joined by a conical outer cone 30 that widens towards the coronal end of the implant body 13 with a cone angle β of about 30°.

The coronal axial end of the implant body 13 is provided with an insertion opening 33 and an adjoining inner cone 35 into which a corresponding outer cone 37 of the neck portion 14 of a replacement tooth is inserted. The cone angle γ of the inner cone 35 is approximately equal to that of the cone angle β, i.e., about 30° in the present embodiment. The outer side of the outer cone 30 may be provided with so-called microgrooves situated in a transversal plane, which improve the adhesion to the jaw bone.

The neck portion 14 of the replacement tooth comprises a cylindrical screw opening 34, into which a replacement tooth retaining element 32 in the form of a retaining screw is inserted, the male thread of the screw being threaded into a corresponding female thread 24 of the implant body 13. The replacement tooth neck portion 14 is thereby fastened on the implant body 13 in a manner secured against rotation.

The crown portion 16 of the replacement tooth is set on an outer cylinder 44 of the neck portion 14 and is fixed in a manner secured against rotation by cementing and/or by a transversal screw connection.

Figure 2:
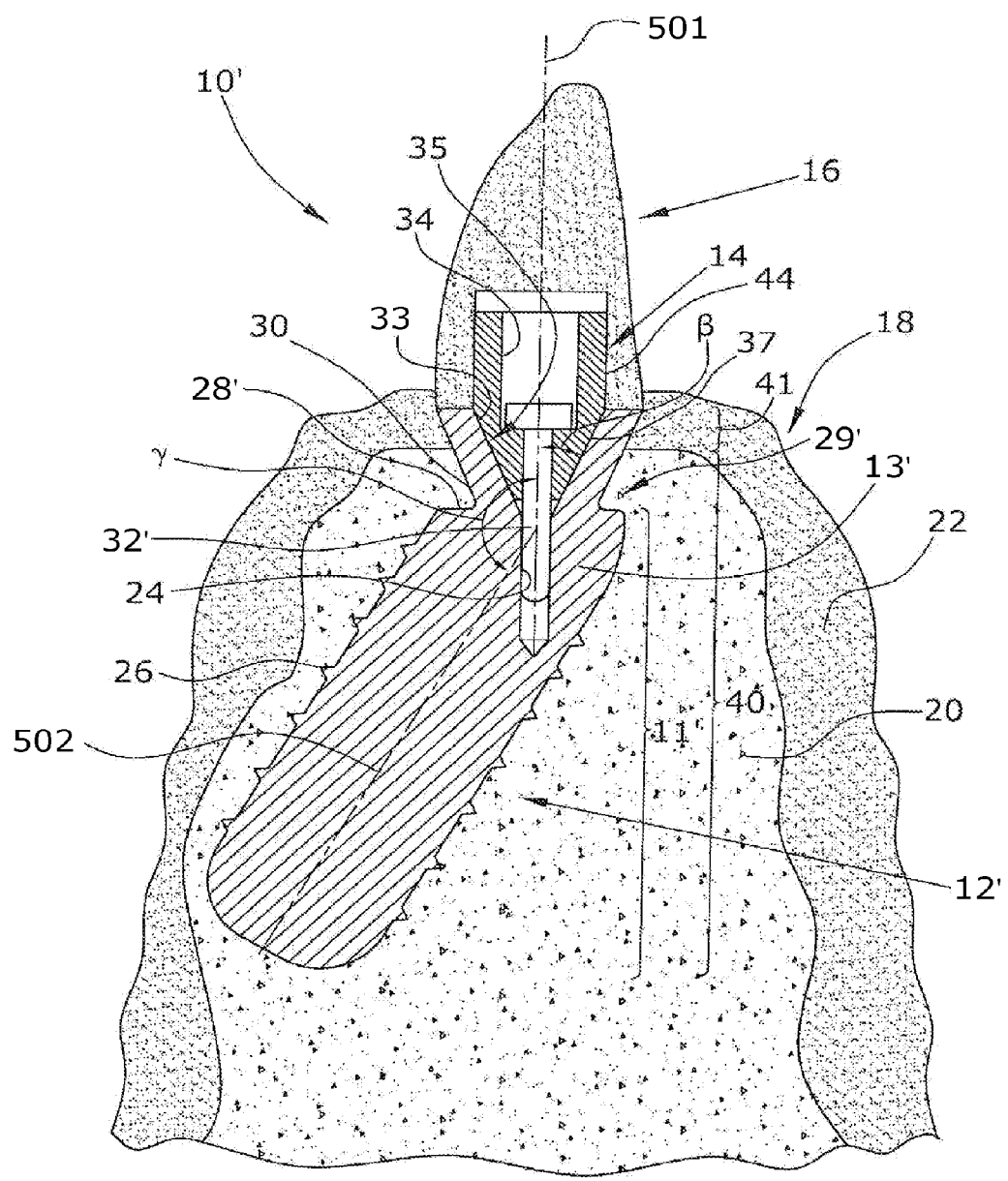
FIG. 2 shows an embodiment of an angled, i.e., a non-linear jaw implant in longitudinal section.

FIG. 2 is a longitudinal section of an embodiment of a dental implant arrangement 10' for insertion in a patients jaw, which, different from the aforementioned embodiment in that it is not linear, but angled. The angle is provided between the radial step 29' and the ingrowth section 11' so that the implant body 13' is at an angle to the insertion opening 33. Such angled jaw implants 12' are required where an implantation parallel to the axial line of the patient's body is not possible because of the course of nerve tracts in the patients jaw. At its coronal end, the ingrowth section 11' terminates in the radial step 29' formed by an annular surface 28'. In this embodiment, the retaining element 32' of the replacement tooth may be a tie-rod whose non-coronal end is anchored, e.g., threaded, in the ingrowth section 11' and whose coronal end is adapted to be tightened axially. The angle of the axial line 501 of the insertion opening with the axial line 502 of the ingrowth section 11' is between 165° and 110°, generally between 160° and 140°.

The present invention is not limited to embodiments described herein; reference should be had to the appended claims.

What is claimed is:

1. A dental jaw implant for supporting at least one of a replacement tooth neck and a crown portion, the dental jaw implant consisting of a monolithic implant body consisting of an ingrowth section and an outer cone:

the ingrowth section comprising an ingrowth structure configured to grow together with a patient's jaw bone;

the ingrowth section having a top surface at a coronal end of the ingrowth section and a non-coronal end defining a non-coronal, terminal end of the implant;

the outer cone extending directly from the top surface of the ingrowth section in a coronal direction and having a top surface defining a coronal, terminal end of the implant;

the outer cone tapering from a wide end at the coronal end of the implant to a narrow end making direct contact with the top surface of the ingrowth section, the wide end being wider than the narrow end;

an insertion opening arranged at the coronal end of the implant, the insertion opening being configured to have the at least one of the replacement tooth neck and the crown portion be inserted therein; and a female thread adjoining the insertion opening, the female thread being configured to thread a replacement tooth retaining element, the replacement tooth retaining element being configured to retain the at least one of the replacement tooth neck and the crown portion, wherein, the top surface of the ingrowth section forms a radial step consisting of one annular surface substantially disposed in a radial plane, the one annular surface being arranged directly between the narrow end of the outer cone and the ingrowth section and facing the coronal end of the implant.

2. The dental jaw implant as recited in claim 1, wherein the insertion opening includes a first axial line, and wherein the radial step forms an angle ($\alpha$) of 70°-100° with respect to the first axial line.

3. The dental jaw implant as recited in claim 2, wherein the angle ($\alpha$) is from 85°-100° with respect to the first axial line.

4. The dental jaw implant as recited in claim 2, wherein the outer cone forms a cone angle ($\beta$) of 10-50° with respect to the first axial line.

5. The dental jaw implant as recited in claim 1, wherein the radial step includes a radial depth, the ingrowth section includes a largest outer radius, and wherein the radial depth is at least one third of the largest outer radius.

6. The dental jaw implant as recited in claim 1, wherein the radial step is disposed in a longitudinal jaw bone section of the monolithic implant body.

7. The dental jaw implant as recited in claim 6, wherein the monolithic implant body includes a longitudinal gingiva section, and wherein the outer cone is at least partly disposed in the longitudinal jaw bone section and at least partly disposed in the longitudinal gingiva section of the monolithic implant body.

8. The dental jaw implant as recited in claim 1, wherein the insertion opening is angled with respect to the ingrowth section.

9. The dental jaw implant as recited in claim 8, wherein the insertion opening includes a first axial line, and the ingrowth section includes a second axial line, and wherein the first axial line forms an angle ($\gamma$) of 165° to 110° with respect to the second axial line.

10. The dental jaw implant as recited in claim 9, wherein the first axial line forms an angle ($\gamma$) of 155° to 125° with respect to the second axial line.

11. A dental jaw implant for supporting at least one of a replacement tooth neck and a crown portion, the dental jaw implant consisting of a monolithic implant body consisting of an ingrowth section and an outer cone:

the ingrowth section comprising an ingrowth structure configured to grow together with a patient's jaw bone, the ingrowth section comprising a cylindrical section comprising a cylindrical section diameter and at least one thread;

the outer cone arranged at a coronal axial end of the cylindrical section and extending from a top surface of the cylindrical section, the outer cone comprising a narrow end arranged at the coronal axial end of the cylindrical section, the outer cone widening outwards from the narrow end to a wide end in a coronal axial direction, the wide end being wider than the narrow end, the wide end forming a coronal, terminal end of the monolithic implant body, the outer cone further comprising an outer cone section diameter at the wide end and an insertion opening, the outer cone section diameter at the wide end being no larger than the cylindrical section diameter, the insertion opening being configured to have the at least one of the replacement tooth neck and the crown portion be inserted therein; and a female thread adjoining the insertion opening, the female thread being configured to thread a replacement tooth retaining element, the replacement tooth retaining element being configured to retain the at least one of the replacement tooth neck and the crown portion, wherein, the top surface of the ingrowth section forms a radial step consisting of an annular surface substantially disposed in a radial plane, the annular surface being formed by the arrangement of the outer cone at the coronal axial end of the cylindrical section.

12. The dental jaw implant as recited in claim 11, wherein the insertion opening includes a first axial line, and wherein the radial step forms an angle ($\alpha$) of 70°-100° with respect to the first axial line.

13. The dental jaw implant as recited in claim 12, wherein the angle ($\alpha$) is from 85°-100° with respect to the first axial line.

14. The dental jaw implant as recited in claim 12, wherein the outer cone forms a cone angle ($\beta$) of 10-50° with respect to the first axial line.

15. The dental jaw implant as recited in claim 11, wherein the radial step includes a radial depth, the ingrowth section includes a largest outer radius, and wherein the radial depth is at least one third of the largest outer radius.

16. The dental jaw implant as recited in claim 11, wherein the radial step is disposed in a longitudinal jaw bone section of the monolithic implant body.

17. The dental jaw implant as recited in claim 16, wherein the monolithic implant body includes a longitudinal gingiva section, and wherein the outer cone is at least partly disposed in the longitudinal jaw bone section and at least partly disposed in the longitudinal gingiva section of the monolithic implant body.

18. The dental jaw implant as recited in claim 11, wherein the insertion opening is angled with respect to the ingrowth section.

19. The dental jaw implant as recited in claim 18, wherein the insertion opening includes a first axial line, and the ingrowth section includes a second axial line, and wherein the first axial line forms an angle ($\gamma$) of 165° to 110° with respect to the second axial line.

20. The dental jaw implant as recited in claim 19, wherein the first axial line forms an angle ($\gamma$) of 155° to 125° with respect to the second axial line.

* * * * *